United States Patent [19]

Yamaguchi et al.

[11] Patent Number: 4,839,020

[45] Date of Patent: Jun. 13, 1989

[54] GAS SENSOR

[75] Inventors: Shuichiro Yamaguchi, Fuji; Norio Daikuhara; Takeshi Shimomura, both of Fujinomiya, all of Japan

[73] Assignee: Terumo Kabushiki Kaisha, Tokyo, Japan

[21] Appl. No.: 53,280

[22] Filed: May 22, 1987

[30] Foreign Application Priority Data

May 26, 1986 [JP] Japan ................. 61-120565

[51] Int. Cl.[4] ............................................. G01N 27/26
[52] U.S. Cl. ................................... 204/431; 204/424; 204/432
[58] Field of Search ................. 204/414, 424, 431, 433

[56] References Cited

U.S. PATENT DOCUMENTS

| 3,926,764 | 12/1974 | Ruzicka et al. | 204/195 |
|---|---|---|---|
| 3,957,612 | 5/1976 | Niedrach et al. | 204/195 |
| 3,957,613 | 5/1976 | Macur | 204/195 |
| 4,052,285 | 10/1977 | Dobson | 204/195 |
| 4,115,209 | 9/1978 | Fraiser et al. | |
| 4,132,616 | 1/1979 | Tanttrom | 204/414 X |
| 4,198,851 | 4/1980 | Janata | 73/23 |
| 4,214,968 | 7/1980 | Battaglia et al. | 204/195 |
| 4,280,889 | 7/1981 | Szonntagh | 204/195 |
| 4,282,079 | 8/1981 | Chang et al. | |
| 4,305,802 | 12/1981 | Koshiishi | 204/195 |
| 4,454,007 | 6/1984 | Pace | 204/1 T |
| 4,473,456 | 9/1984 | Hawkins | 204/414 |
| 4,512,870 | 4/1985 | Kohara et al. | 204/416 |
| 4,549,951 | 10/1985 | Knudson et al. | 204/416 |
| 4,561,962 | 12/1985 | Kankare | |
| 4,563,263 | 1/1986 | Oyama et al. | 204/418 |
| 4,615,954 | 10/1986 | Solomon et al. | 429/27 |
| 4,632,732 | 12/1986 | Fog et al. | 204/1 T |
| 4,700,709 | 10/1987 | Kraig | 204/431 X |

FOREIGN PATENT DOCUMENTS

| 01186210 | 7/1986 | European Pat. Off. |
| 3134760A | 9/1982 | Fed. Rep. of Germany |
| 52-30490 | 8/1977 | Japan |
| 59164952 | 9/1981 | Japan |
| 57-63444 | 4/1982 | Japan |
| 57-196116 | 12/1982 | Japan |
| 85167951 | 10/1983 | Japan |
| 59-57156 | 4/1984 | Japan |
| 60-7357 | 1/1985 | Japan |
| 60-52759 | 3/1985 | Japan |
| 60-73351 | 4/1985 | Japan |
| 898314 | 1/1982 | U.S.S.R. |

OTHER PUBLICATIONS

Oyama et al "Electrochemical Properties of Electropolymerized Poly (1-pyrenamine) Films", The Chemical Society of Japan, Jul. 1986.
T. H. Ryan, "Electrochemical Detectors", p. 7.
Ma et al, "Organic Analysis Using Ion-Sensitive Electrodes", vol. 2, pp. 60 & 62.
Tamura et al, "Coated Wire Sodium- and Potassium-Electrodes Based on Bis(crown ether) Compounds", *Analytical Chemistry*, vol. 54, No. 7, Jun. 1982, pp. 1224–1427.
Wuthier et al, "Tin Organic Compounds as Neutral Carriers for Anion Selective Electrodes", *Analytical Chemistry*, vol. 56, No. 3, Mar. 1984, pp. 535–538.
Norov et al, "Calcium-Selective Electrode Without an
(List continued on next page.)

*Primary Examiner*—Stephen J. Kalafut
*Attorney, Agent, or Firm*—Burns, Doane, Swecker & Mathis

[57] ABSTRACT

A gas sensor includes a multi-layered solid-state pH electrode and a reference electrode coated with a gas-sensitive layer (solid-state or gel-state) sensitive to an ion of interest, the surface of the combination being coated with a gas-permeable layer. Also provided in a gas sensor having a pH electrode and a reference electrode immersed in a gas-sensitive solution within a gas-permeable layer. Preferably, a fixed distance is maintained between a sensitive portion of the pH electrode, a sensitive portion of the reference electrode and the gas-permeable layer isolated by means of a porous layer. In another emodiment, the gas sensor incorporates a common electrode and a thermister for temperature calibration.

14 Claims, 7 Drawing Sheets

OTHER PUBLICATIONS

Internal Reference Solution", *Journal of Analytical Chemistry*, vol. 34, No. 8, Part 1, Aug. 1979.

Oyama et al, "Ion Selective Electrode Prepared By Modifying an Electrode With Polymers", *Tokyo Seminar on Macromolecular Complexes*, Tokyo Univ., Oct. 14–17, 1987.

Oyama et al, "Hydrogen Ion Selective Microelectrode Prepared by Modifying An Electrode With Polymers", *Analytical Chemistry*, 1987, vol. 59, pp. 258–262 Jan. 1987.

Oyama, "Ion Selective Microelectrode Prepared By Modifying an Electrode With Polymers", *International Electrical Symposium*, Schaumberg, Ill., May 27–29 (1987), pp. 122–125.

Oyama et al, "A New Type of Ion-Selective Microelectrodes Using Electropolymerized Thin Films", j-4 *Bioelectroanalytical Chemistry Symposium*, Honolulu, Hawaii, Oct. 18–23, 1987.

Ammann, "Ion-Selective Microelectrodes", Principles, Design & Application, pp. 5–7, 66 & 100.

GAS SENSOR

BACKGROUND OF THE INVENTION

1. Field of the Invention:

This invention relates to a gas sensor capable of stably measuring gas concentration or gas partial pressure in a solution, living body or gas by the potentiometric response of an electrode. More particularly, the invention relates to a gas sensor for measuring carbon dioxide, ammonia gas, etc.

2. Description of the Prior Art:

A glass electrode is well-known as a gas sensor for sensing such gases as carbon dioxide gas and ammonia gas. The glass electrode has a thin internal solution layer retained between the sensitive portion of a pH sensor and a gas-permeable layer. Gas molecules which pass through the gas-permeable layer dissolve in the internal solution and change the pH thereof, which change is sensed by the pH sensor. However, since the electrode used in a sensor of this type is a glass electrode, the sensor breaks easily and is difficult to miniaturize. To eliminate these drawbacks, the inventors have disclosed a number of solid-state pH sensors, as described in the specifications of Japanese Patent Publication Nos. 59-281076, 60-35691, 60-53308 and 60-93176.

However, it has been found that even a gas sensor employing the aforementioned solid-state pH sensor experiences a deterioration in the ionic characteristics (particularly the ion sensitivity) of its electrode about one month. Another disadvantage is that the gas sensor is not suited to continuous monitoring because of a slow response with regard to the change in solution temperature.

SUMMARY OF THE INVENTION

An object of the present invention is to provide a miniature, sturdy solid-state gas sensor capable of in vivo measurement and exhibiting stable ionic characteristics over an extended period of time.

Another object of the present invention is to provide a miniature gas sensor for measuring the concentration of a gas in a solution, which sensor solves problems associated with miniaturization and problems related to temperature compensation due to use in a system where solution temperature varies, thereby making it possible for the gas sensor to perform continuous monitoring in a living body.

The foregoing objects are attained by providing a gas sensor comprising: a pH electrode which includes an electrically conductive substrate, a redox layer coating a surface of the electrically conductive substrate, and a hydrogen ion carrier layer coating a surface of the redox layer; a reference electrode; an insulating layer for insulating the pH electrode and the reference electrode; a gas-sensitive layer coating exposed surface portions of the pH electrode, the insulating layer and the reference electrode; and a gas-permeable layer coating a surface of the gas-sensitive layer.

In another embodiment of the invention, there is provided a gas sensor comprising: a pH electrode having a sensitive portion; a reference electrode having a sensitive portion; and a gas-permeable layer contacting the sensitive portion of the pH electrode and the sensitive portion of the reference electrode through the intermediary of a gas-sensitive solution.

In further embodiment of the invention, there is provided a gas sensor comprising: a pH electrode having a sensitive portion; a reference electrode having a sensitive portion; a thermister; and a gas-permeable layer contacting the sensitive portion of the pH electrode, the sensitive portion of the reference electrode and the thermister through the intermediary of a gas-sensitive solution.

Thus, whereas the conventional gas sensor is assembled with a gas-permeable membrane, a liquid gas-absorption chamber and a glass electrode, the present invention provides a solid-state gas sensor in which a gas-sensitive layer (solid-state or gel-state) is furnished between a hydrogen ion carrier layer and a gas-permeable membrane. As a result, the sensor can be miniaturized and will not readily break. Moreover, an electrolyte contained in the gas-sensitive layer can be selected over a wide range in accordance with the gas ion of interest, which has a close connection to the metabolism of a living body. Therefore, by being combined with a guide wire, catheter or the like, the gas sensor can be employed as a medical gas sensor for in vivo measurement of gas concentration. The gas sensor of the invention does not exhibit any change in sensor characteristics even 42 days after manufacture.

Furthermore, since the gas sensor of the invention has a porous layer disposed between the gas-permeable layer and hydrogen ion carrier layer, the sensor characteristics have good reproducibility and an excellent speed of response is attained. In addition, by providing the sensor with an internal thermister, a temperature-compensated measurement is possible in a system where temperature varies. This makes highly precise measurement possible.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

FIG. 1 (a) is a sectional view illustrating a first embodiment of a gas sensor according to the present invention;

FIG. 1 (b) is a view showing a pH electrode portion constituting the gas sensor shown in FIG. 1 (a);

FIG. 2 (a) is a sectional view illustrating a second embodiment of a gas sensor according to the present invention;

FIG. 2 (b) is a view showing a pH electrode portion constituting the gas sensor shown in FIG. 2 (a);

FIG. 3 (a) is a schematic view illustrating the construction of gas sensor according to another embodiment of the invention;

FIG. 3 (b) is a schematic view illustrating the construction of a reference electrode used in the gas sensor of FIG. 3 (a);

FIGS. 8 (a)–(c) are graphs, based on the results of measurements, showing relationships among time, partial pressure, electric potential and temperature.

DESCRIPTION OF THE PREFERRED EMBODIMENTS

The present invention will now be described in detail based on preferred embodiments thereof.

Figure 1:
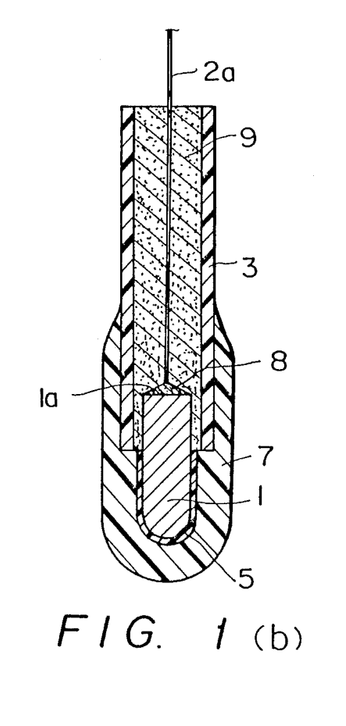

The characterizing features of the invention will become clear with reference to FIGS. 1 (a), (b) and Table 1.

FIG. 1 (a) is a view showing the construction of a gas sensor according to an embodiment of the present invention, and FIG. 1 (b) is a view showing a pH electrode portion constituting the gas sensor of FIG. 1 (a). A pH electrode lead wire 2a consisting of Teflon-coated copper wire having a diameter of 0.2 mm is fixed by means of an electrically conductive bonding agent 8 to the bottom surface 1a of an electrically conductive substrate 1 having a diameter of 1.1 mm and a length of 3.0 mm. The outer periphery of the electrically conductive substrate 1 is sheathed and insulated by heat-shrinkable tubing 3 so as to leave the tip of the substrate exposed to a length of 1.5 mm, and the tubing is fixed by an epoxy resin 9. The exposed tip of the electrically conductive substrate 1 is ground and polished into a hemispherical shape, with the surface area of the exposed portion being adjusted to 0.064 cm². A redox layer 5 is formed on the exposed surface of the substrate 1 by electrolytic oxidative polymerization. Thus is formed an electrode having the redox layer 5 covering the electrically conductive substrate 1.

The electrically conductive substrate used in the gas sensor of the invention may consist of an electrically conductive carbon material such as basal-plane pyrolytic graphite (hereafter referred to as "BPG") or glassy carbon, a metal such as gold, platinum, copper, silver, palladium, nickel or iron, especially a precious metal, or a composite obtained by coating the surface of any of these metals with a semiconductor such as indium oxide or tin oxide. The electrically conductive carbon material is preferred, especially BPG. In order to make the conductive substrate small in size, a stick-shaped member is used and a membrane having a redox function is deposited over an area of 1-20 mm² on the outer circumferential surface of the stick-shaped substrate or on its outer circumferential surface and tip surface. A lesser area is undersirable as it will cause the electrode membrane resistance of the ion carrier membrane to exceed 50 MΩ at 10° C.; a larger area will result in an gas sensor which is no longer small in size. Though the stick-shaped substrate may be of a cylindrical, prismatic or like configuration, the cylindrical substrate having a rounded tip is especially preferred in terms of moldability and membrane adhesion. Conventionally, the basal plane of BPG is utilized as the electrode plane. However, the inventor has discovered that the edge plane of BPG can also be effectively exploited, and that because of this, a stick-shaped electrode can be fabricated even from BPG. BPG is highly preferred since it excels in terms of sensor operating stability. A stick of BPG, for example of the cylindrial shape, will exhibit excellent strength especially if the diameter selected is 0.1-2 mm.

The redox layer refers to one in which an electrode comprising an electrically conductive substrate having this layer deposited on its surface is capable of generating a constant potential on the substrate owing to a redox reaction. In the present invention, an especially preferred redox layer is one which will not allow the potential to fluctuate due to the partial pressure of oxygen gas. Particularly suitable examples of the redox layer are (1) an organic compound membrane or a polymeric membrane capable of a quinone-hydroquinone type redox reaction, and (2) an organic compound membrane or polymeric membrane capable of an amine-quinoid type redox reaction. (3) poly (pyrrole) and poly (thionylene) compound type electro conductive substrates. The quinone-hydroquinone type redox reaction is expressed by e.g. the following reaction formula, taking a polymer as an example:

where $R_1$, $R_2$ represent e.g. compounds having a structure containing an aromatic series.

The amine-quinoid type redox reaction is expressed by e.g. the following reaction formula, taking a polymer as an example:

where $R_3$, $R_4$ represent e.g. compounds having a structure containing an aromatic series.

The following compounds (a)–(d) can be mentioned as compounds capable of forming the abovementioned layer having the redox function:

(a) A hydroxy aromatic compound expressed by where $Ar_1$ represents an aromatic nucleus, $R_5$ a substituent group, $m_2$ is 1 to the effective valence of $Ar_1$, and $n_2$ is 0 to the effective valence of $Ar_{Ar1}$ minus 1.

The aromatic nucleus of $Ar_1$ may be a single ring such as a benzene nucleus, a multiple ring such as an anthracene nucleus, pyrene nucleus, chrysene nucleus, perylene nucleus or coronene nucleus, or a heterocyclic ring. Examples of the substituent group $R_5$ are alkyl groups such as a methyl group, aryl groups such as a phenyl group, and a halogen atom. More specifically, examples are dimethyl phenol, phenol, hydroxy pyridine, o- and m-benzyl alcohols, o-, m- and p-hydroxybenzaldehydes, o- and m-hydroxyacetophenones, o-, m- and p-hydroxypro-piophenons, o-, m- and p-hydroxybenzophenones, o-, m- and p-carboxyphenols, diphenylphenol, 2-methyl-8-hydroxy-quinoline, 5-hydroxy-1, 4-naphtoquinone, 4-(p-hydroxy-phenyl)2-buthanone, 1,5-dihydroxy-1, 2, 3, 4-tetra-hydronaphthalene, bisphenol-A, salicylanilide, 5-and 8-hydroquinoines, 1,8-dihydroxyanthraquinone, and 5-hydroxy-1,4-naphthoquinone.

(b) An amino aromatic compound expressed by the formula where $Ar_2$ represents an aromatic nucleus, $R_6$ a substituent group, $m_3$ is 1 to the effective valence of $Ar_2$, and $n_3$ is 0 to the effective valence of $Ar_2$ minus 1.

As for the aromatic nucleus $Ar_2$ and the substitution group $R_6$, items similar to $Ar_1$ and the substitution group $R_5$ in compound (a) can be used. Specific examples of the amino aromatic compound are aniline, 1,2-diaminobenzene, aminopyrene, diaminopyrene, aminochrysene, diaminochrysene, 1-aminonaphtholene, 9-aminonaphtholene, 9, 10-diaminonaphtholene, 1-aminoanthraquinone, p-phenoxyaniline, o-phenylenediamine, p-chloroaniline, 3, 5-dichloroaniline, 2, 4, 6-trichloroaniline, N-methylaniline, and N-phenyl-p-phenylenediamine and so on.

(c) A quinone such as 1,6-pyrenequinone, 1,2,5,8-tetrahydroxynalizaline, phenanthrenequinone, 1-aminoanthraquinone, purpurine, 1-amino-4-hydroxynthraquinone, and anthralphyne.

Among these compounds, 2,6-xylenol and 1-aminopyrene are especially preferred.

(d) Pyrrole and derivatives thereof (e.g. N-methyl pyrrole), and thiophene and derivatives thereof (e.g. methyl thiophene).

Further, examples of compounds capable of forming the layer having the redox function are those which undergo a redox reaction. The following can be mentioned: poly(N-methyl aniline) [Onuki, Matsuda, Oyama, Nihon Kagakukaishi, 1801-1809 (1984)], poly(2,6-dimethyl-1,4-phenylene ether), poly(o-phenylediamine), poly(phenol) and polyxylenol; organic compounds containing the compounds (a) through (d) such as pyrazoroquinone group-containing vinyl compound-polymers, isoaroxythazine group-containing vinyl compound-polymers and other quinone group-containing compound-polymers, lower polymeric compounds (oligomers) of compounds (a) through (d), or substances obtained by fixing the compounds of (a) through (d) to polymeric compounds such as polyvinyl compounds and polyamide compounds. In the present specification, the term "polymer" is taken to mean both homopolymers and mutual polymers such as copolymers.

In the present invention, in order to deposit the compound capable of forming the redox layer on the an electrically conductive substrate, a polymer obtained by synthesizing an amino aromatic compound, a hydroxy aromatic compound or the like on an electrically conductive substrate of electrically conductive carbon or a precious metal by an electrolytic oxidation polymerization method or electrodeposition method, or a polymer synthesized by application of electron beam irradiation, light or heat, is dissolved in a solvent. The resulting solution is (a) deposited on electrically conductive substrate by painting or dipping, (b) reacted in the gas phase in vacuo and deposited directly on the an electrically conductive substrate, or (c) irradiated with light, heat or radiation to be deposited directly on the electrically conductive substrate. Among these three methods, the most preferred is that in which, electrooxidation polymerization method. The electrolytic oxidation polymerization method is implemented by subjecting the amino aromatic compound or hydroxy aromatic compound to electrolytic oxidation polymerization in a solvent in the presence of a suitable supporting electrolyte and depositing a layer of the polymer on the surface of the electrically conductive substrate. Preferred examples of the solvent are acetonitrile, water, dimethyl formamide, dimethyl sulfoxide, propylene carbonate, methanol and the like. Preferred examples of the supporting electrolyte are sodium perchlorate, sulfuric acid, sodium sulfate, phosphoric acid, boracic acid, tetrafluoro-potassium phosphate, quaternary ammonium salts and the like.

The membrane thickness of the redox layer is 0.01 $\mu$m -1.0 mm, preferably 0.1 $\mu$m -0.1 mm. A membrane thickness of less than 0.01 $\mu$m does not fully bring forth the effects of the invention, while a thickness of more than 1.0 mm is undesirable from the viewpoint of miniaturizing the sensor.

The redox layer used in the present invention can be used in a form impregnated with an electrolyte. Examples of the electrolyte are phosphoric acid, dipotassium hydrogen phosphate, sodium perchlorate, sulfuric acid, tetrafluoro borate, tetraphenyl borate and the like. In order to impregnate the redox layer with the electrolyte, a simple method which can be adopted is to coat the electrically conductive substrate with the redox layer and then dip the resulting membrane into a solution of the electrolyte.

The outer surface of the aforementioned electrode is coated with a hydrogen ion carrier layer 7. Employed as the layer 7 is a membrane including a polymeric compound carrying an ion carrier substance for the ion of interest and, if necessary, an electrolyte.

The following are examples of the ion carrier material which can be used, depending upon the ion of interest:

(i) For hydrogen ion

Examples of a hydrogen ion carrier material are amines expressed by the formula (where $R^7$, $R^8$, $R^9$ represent the same or different alkyl groups, among which at least two alkyl groups have a carbon number of 8-18), and compounds expressed by the formula (where $R^{10}$ represents an alkyl group having a carbon number of 8-18). Tri-n-dodecylamine is especially preferred.

Examples of the electrolytic salt are sodium tetrakis (p-chlorophenyl) borate, potassium tetrakis (p-chlorophenyl) borate, and a compound expressed by the formula (R$_{18}$)$_4$NBF$_4$ where $R_{18}$ represents an alkyl group, preferably an alkyl group having a carbon number of 2-6.

Potassium tetrakis (p-chlorophenyl) borate is especially suited for use to hydrogen ion, potassium ion, sodium ion and hydrogencarbonate ion. Tetrachloroborate is to chlorine ion. Di-(n-octylphenyl) phosphate is to calcium ion.

Examples of the polymer compound which holds ion carrier material are organic polymer compounds such as vinyl chloride resin, vinyl chloride-ethylene copolymer, polyester, polyacryl amide and polyurethane, and inorganic polymer compounds such as silicone resin. Vinyl chloride is especially preferred. Compounds are used in which the plasticizer does not readily elute. Examples of such a plasticizer are dioctyl sebacate ester, dioctyl adipate ester, dioctyl maleate ester and di-n-octyl phenylphosphonate. Dioctyl sebacate and di(2-ethylhexyl) sebacate are expecially preffered.

Tetrahydrofuran (THF) is especially preferred for use as solvent. In order to coat the surface of the barrier layer with the ion-sensitive layer having the foregoing composition, the polymer compound, the plasticizer, the ion carrier material and the electrolytic salt are dissolved in a solvent (e.g. tetrahydrofuran). The electrically conductive substrate coated by the barrier layer is repeatedly dipped into the resulting solution followed by drying to adjust thickness. It is desired that the thickness of the applied ion-sensitive layer be 0.1 μm–10 mm, preferaby 0.4–2.0 mm.

A reference electrode 4 is fabricated as follows: First, about 50 mm of silver wire having a diameter of about 0.2 mm is wound on the tubing 3 at a distance of about 5 mm from the end of the coated hydrogen ion carrier layer 7. The remaining wire is used as a reference electrode lead wire 2b, a portion of which is insulated by being coated Teflon resin. A portion of the lead wire 2b is fixed to the heat-shrinkable tubing 3 by epoxy resin. Next, constant-current electrolysis (30 mA/cm$^2$ for 40 min) is carried out in a 0.1 M sodium chloride, 0.01 M sodium hydroxide solution to form a silver chloride film on the exposed portion of the silver. The result is the reference electrode 4. The pH electrode and reference electrode 4 are thus integrated.

Next, a gas-sensitive layer 6 is formed coating the exposed surface of the reference electrode 4, the exposed surface of the pH electrode and the exposed surface of the heat-shrinkable tubing 3. The gas-sensitive layer 6 is formed in a manner which will now be described.

Examples of materials which can be used to form the gas-sensitive layer are a polymeric cellulose derivative possessing an electrolytic solution or aqueous solution, an aqueous polymer and the like. Particularly preferred is a layer of polyvinyl alcohol (PVA). Coating the aforementioned exposed surfaces redox layer with the gas-sensitive layer 6 is accomplished by e.g. preparing a 10% aqueous solution of PVA by dissolving PVA (having a polymerization degree of about 2000) in a solvent which contains a salt of the gas ion of interest, dipping the integrated electrode comprising the pH electrode and reference electrode 4 in this solution, lifting the electrode from the solution and then drying it at 150° C., thereby obtain the gas-sensitive layer 6 containing the gas ion of interest. These preferred thickness of the gas-sensitive layer 6 is 100 μm.

The electrolytic salt contained in the gas-sensitive layer 6 should be selected depending upon gas on interest. Preferably, sodium bicarbonate - sodium chloride is used to detect carbon dioxide gas, ammonium chloride - sodium chloride to detect ammonia gas, sodium nitrite to detect nitrogen dioxide gas, sodium bisulfate to detect sulfur dioxide gas, and sodium acetate to detect acetic acid gas.

The gas-sensitive layer 6 is coated with a gas-permeable layer 10. This is carried out by preparing a solution in which a silicone membrane composition is dissolved as a solvent, and dipping the intergrated electrode, which has been coated with the gas-sensitive layer 6, into the solution. The gas-permeable layer 10 preferably has a thickness of 1 μm–1 mm, with 10 μm–300 μm being especially preferred. It is also preferred that the gas-permeable layer 10 be hydrophobic.

Five gas sensors each for a different gas of interest were prepared as Examples 1 through 5, in which the redox layers and hydrogen ion carrier layers were the same throughout.

EXAMPLE 1 (CARBON DIOXIDE GAS SENSOR)

| Redox Layer | |
|---|---|
| Thickness: | 30 μm |
| Composition: | |
| 2,6-dimethylphenol | 0.5 M |
| sodium perchlorate | 0.2 M |
| solvent: acetonitrile | |
| Hydrogen Ion Carrier Layer | |
| Thickness: | 1.0 mm |
| Composition: | |
| tridodecylamine | 10 mg/ml |
| tetrakis(p-chlorophenyl) potassium borate | 1.25 mg/ml |
| polyvinyl chloride ($P_n$ = 1050) | 81.2 mg/ml |
| dioctyl sebacate (DOS) | 160 mg/ml |
| solvent: tetrahydrofuran (THF) | 4 ml |
| Gas-Sensitive Layer | |
| Thickness: | 0.1 mm |
| Composition: | |
| 10% polyvinyl alcohol (PVA) | |
| Solvent: | |
| $NaHCO_3$ | 5 mM |
| NaCl | 0.15 M |

EXAMPLE 2 (AMMONIA GAS SENSOR)

| Gas-Sensitive Layer | |
|---|---|
| Thickness: | 0.1 mm |
| Composition: | |
| 10% polyvinyl alcohol (PVA) | |
| Solvent: | |
| $NH_4Cl$ | 10 mM |
| NaCl | 0.15 M |

EXAMPLE 3 (NITROGEN DIOXIDE GAS SENSOR)

| Gas-Sensitive Layer | |
|---|---|
| Thickness: | 0.1 mm |
| Composition: | |
| 10% polyvinyl alcohol (PVA) | |
| Solvent: | |
| $NaNO_2$ | 10 mM |
| NaCl | 0.15 M |

EXAMPLE 4 (SULFUR DIOXIDE GAS SENSOR)

| Gas-Sensitive Layer | |
|---|---|
| Thickness: | 0.1 mm |
| Composition: | |
| 10% polyvinyl alcohol (PVA) | |
| Solvent: | |
| $NaHSO_4$ | 10 mM |
| NaCl | 0.15 M |

EXAMPLE 5 (ACETIC ACID GAS SENSOR)

| Gas-Sensitive Layer | |
|---|---|
| Thickness: | 0.1 mm |
| Composition: | |
| 10% polyvinyl alcohol (PVA) | |
| Solvent: | |
| $CH_3COONa$ | 100 mM |
| NaCl | 0.15 M |

<Experiment 1>

Figure 2A:
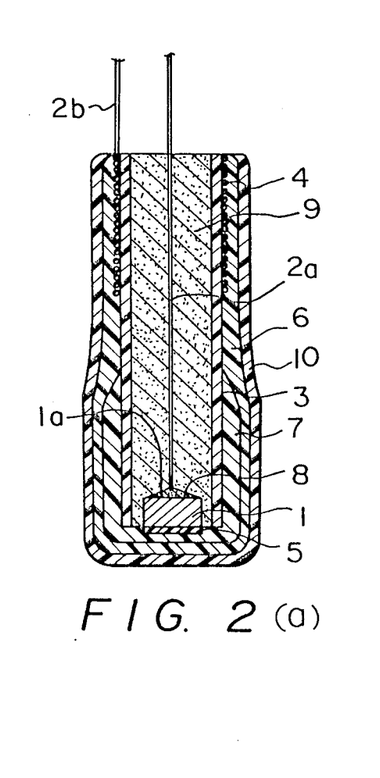
Figure 2B:
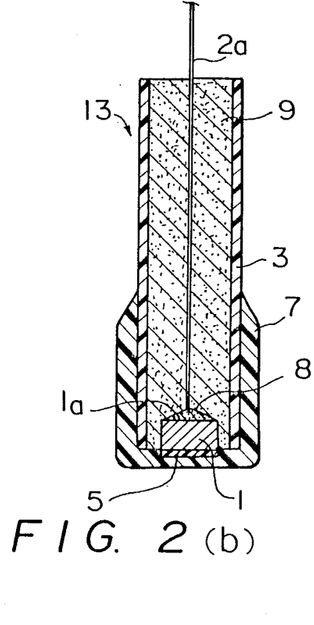
Figure 3:
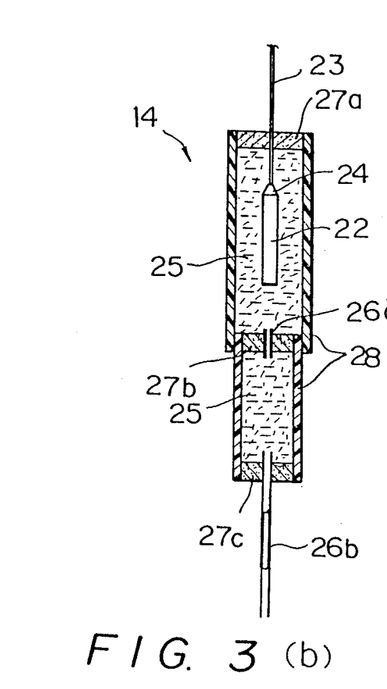

The gas sensors fabricated in the above Examples were subjected to experimentation. The partial pressure of the gas in a phosphate buffer solution was measured at 37° C. based on a change in emf across the gas sensor used as the active electrode and an internal reference electrode (Ag/AgC1). The relationship between electromotive force and gas partial pressure was obtained in the form of a logarithmic plot. The slope of the Nernst plot was investigated. The results are shown in Table 1.

of a reference electrode used in the gas sensor of FIG. 3 (a). Note that the pH electrode is similar in construction and configuration to that of FIG. 2 (b).

(1) Fabrication of carbon electrode

A cylinder 1 having a diameter of 1.0 mm and a length of 3.0 mm was cut from a plate of graphite carbon (EG-51, manufactured by Nihon Carbon), and one end of the cylinder was bonded to the lead wire 2a (the Teflon-coated copper wire) by the electrically conductive bonding agent 8. The other end of the cylinder was ground and polished into a smooth, circular, planar end face. The surface area of the exposed carbon was $7.9 \times 10^{-3}$ cm$^2$. The end of the cylinder 1 having the lead wire 2a attached thereto was inserted into the Teflon tubing 3, having an inner diameter of 1.10 mm and an outer diameter of 1.50 mm, and the lead wire was insulated with the epoxy resin bonding agent 9 (TB2067, manufactured by Three Bond Corp.). This completes the fabrication of the carbon electrode.

(2) Application of redox layer 5 by electrode polymerization

An electrolytic oxidative polymerization reaction was carried out under the following conditions using

TABLE 1

| | Examples | | | | |
|---|---|---|---|---|---|
| | 1 | 2 | 3 | 4 | 5 |
| Redox Layer Thickness (Redox Layer Electrolyte Composition) | 30 μm | 30 μm | 30 μm | 30 μm | 30 μm |
| 2,6 xylenol | 0.5 M | 0.5 M | 0.5 M | 0.5 M | 0.5 M |
| sodium perchlorate | 0.2 M | 0.2 M | 0.2 M | 0.2 M | 0.2 M |
| | (Solvent: Acetonitrile, Electrolysis Reaction Temp. $-20°$ C.) | | | | |
| Hydrogen (on Carrier Layer Thickness | 1.0 mm | 1.0 mm | 1.0 mm | 1.0 mm | 1.0 mm |
| (Hydrogen (on Carrier Layer Composition | | | | | |
| tridodecylamine | 10 mg/ml | 10 mg/ml | 10 mg/ml | 10 mg/ml | 10 mg/ml |
| tetrakris (p-chlorophenyl) potassium borate | 1.25 mg/ml | 1.25 mg/ml | 1.25 mg/ml | 1.25 mg/ml | 1.25 mg/ml |
| polyvinyl chloride ($P_n$ = 1050) | 81 mg/ml | 81 mg/ml | 81 mg/ml | 81 mg/ml | 81 mg/ml |
| dioctyl sebacate (DOS) | 160 mg/ml | 160 mg/ml | 160 mg/ml | 160 mg/ml | 160 mg/ml |
| | (Solvent: Tetrafuran (THF) 4 ml) | | | | |
| Barrier Layer Thickness | 0.1 mm | 0.1 mm | 0.1 mm | 0.1 mm | 0.1 mm |
| Barrier Layer Dipping Solution | 10% PVA | 10% PVA | 10% PVA | 10% PVA | 10% PVA |
| Composition Solvent | 5 mM NaHCO$_3$ | 10 mM NH$_4$Cl | 10 mM NaNO$_2$ | 10 mM NaHSO$_4$ | 100 mM CH$_3$COONa |
| | 0.15 M NaCl | 0.15 M NaCl | 0.15 M NaCl | 0.15 M NaCl | 0.15 M NaCl |
| (Nernst Plot Slope: 37° C.) | mV/log[pCO$_2$] | mV/log{[NH$_3$/M]} | mV/log[pNO$_2$] | mV/log[pSO$_2$] | mV/log[pCH$_3$COO] |
| 1 Day After Fabrication | 60.8 | 60.0 | 59.7 | 61.2 | 58.4 |
| 7 Days After Fabrication | 61.0 | 60.5 | 60.1 | 61.1 | 59.8 |
| 40 Days After Fabrication | 61.0 | 60.8 | 60.5 | 60.2 | 60.3 |
| Gas of Interest | Carbon Dioxide Gas | Ammonia Gas | Nitrogen Dioxide Gas | Sulfur Dioxide Gas | Acedic Acid Gas |
| Detection Range | | $10^{-4} \sim 10^{-1}$ M | $10^{-6} \sim 10^{-1}$ M | $10^{-5} \sim 10^{-1}$ M | $10^{-2} \sim 1$ M |

The gases of interest in Table 1 are closely related with the metabolism of a living body. It should be noted, however, that the gas sensor of the invention is not limited to these gases. Furhter, FIG. 2 (a) illustrates a gas sensor having a different configuration, and FIG. 2 (b) illustrates the pH electrode thereof.

The results for each of the Examples 1-5 show that the slopes of the Nernst plot agree with the theoretical value of 61.55 mV/pH 40 days after the fabrication of the gas sensor. A 95% speed of response was found to be less than 2 min.

Experiment 6

FIG. 3 (a) is a view showing the construction of a gas sensor according to another embodiment of the invention, and FIG. 3 (b) is a view showing the construction the aforementioned carbon electrode as the active electrode, a reference electrode (saturated sodium chloride electrode, referred to as an "SSCE") and an opposing electrode (platinum mesh):

Electrolyte:
  0.5 M 2,6-dimethylphenol
  0.2 M sodium perchlorate acetonitrile solvent
Electrolytic temperature: $-20°$ C.
Electrolytic conditions: After the electrode potential was swept three times from 0 V to 1.5 V vs. the SSCE at a sweep rate of 50 mV/sec, an electrolytic reaction was allowed to occur at 1.5 V vs. the SSCE for 10 min.

As a result of this electrolytic polymerization, the redox layer 6 consisting of poly (2,6-xylenol) was formed on the exposed surface of the BPG substrate to a thickness of about 30 μm.

(3) Application of hydrogen ion carrier layer 7

The membrane obtained as described above was dipped into a hydrogen ion carrier having the composition shown in Table 2, the electrode was lifted from the composition and then dried. This procedure was repeated 15 times to uniformly coat the surface of the redox layer 5 with the hydrogen ion carrier layer 7 having a thickness of 1.00 mm.

TABLE 2

| (Hydrogen Ion Carrier Composition) | |
| --- | --- |
| Tridodecylamine | 40 mg |
| Tetrakis(p-chlorophenyl) potassium borate | 6 mg |
| Polyvinyl chloride | 325 mg |
| Dioctyl sebacate (DOS) | 650 mg |
| Tetrahydrofuran (solvent) | 4 ml |

The above-described membrane electrode serves as the active electrode (pH electrode 13) of the gas sensor.

(4) Fabrication of reference electrode

Silver choride and silver oxide were mixed at a ratio of 60:40 in terms of percent by weight and the mixture was pulverized into a finely divided powder. This was then packed and compacted in a jig having a 1 mm-diameter hole to be formed into a cylinder having a diameter of 1 mm and a length of 3 mm. The cylinder was then sintered in an electric oven for 15 min at a temperature of 400° C. A silver wire 23 was bonded to one end of the cylinder 22 by an electrically conductive bonding agent 24 (C-856-06, manufactured by Amicon Corp.).

A Teflon tube 28 having an inner diameter of 1.10 mm and an outer diameter of 1.50 mm was prepared, as shown in FIG. 3 (b). The interior of the tube 28 was filled with an agar-agar gel 25 containing saturated sodium chloride and a silver chloride solution. Fixed to the tube 28 and partitioned therefrom by a urethane bonding agent 27b was a regenerated cellulose hollow fiber (TAF fiber) 26a. The electrode was inserted into one end of the Teflon tube 28 and was fixed thereto by a urethane bonding agent 27a. The other end of the tube, while still filled with the agar-agar gel, 25, was fixed to a regenerated cellulose hollow fiber (TAF fiber) 26b by a urethane bonding agent 27c. Thus was fabricated the reference electrode 14.

(5) Preparation of internal gel 18

An internal gel 18 was prepared as an internal electrolyte solution by dissoving 10 wt-% of polyvinyl alcohol (degree of polymerization: 2000) in an aqueous solution of 10 mM sodium bicarbonate and 154 mM sodium chloride.

(6) Fabrication of gas-permeable layer 16

A dipping solution was prepared by mixing a silicone gel (adhesive silicone type A, manufactured by Dow-Corning) and hexane at a ratio of 33:64 in terms of percent by weight. A Teflon rod having a diameter of 2.8 mm was dipped in the solution and dried, this being repeated four times deposite a silicone film having a thickness of about 70 μm. The Teflon rod was then dipped in freon and the silicone film was peeled off the rod. This film was used as a gas-permeable layer 16.

(7) Fabrication of carbon dioxide gas sensor

The individually prepared components described above were combined in the following manner: First, a Teflon tube 17 having an inner diameter of 2.8 mm and an outer diameter of 3.0 mm was covered with the gas-permeable membrane 16 fabricated in (6) above, a nylon mesh 15 (manufactured by Radiometer) having a thickness of 20 μm or a sheet of Joseph paper was placed on the bottom of the Teflon tube to serve as a spacer, and the internal gel 18 prepared in (5) above was charged into the Teflon tube 17. Next, the pH electrode 13 fabricated in (3), the reference electrode 14 fabricated in (4), and a thermister 20 were inserted into the Teflon tube 17, and these were fixed with an insulator 21 such as an epoxy bonding agent. Thus was fabricated a carbon dioxide gas sensor. The above electrode structure is shown in FIG. 3 (a).

A plug (electrode housing) 19 is for installing the gas sensor in a flow cell for continuous monitoring in a circulating circuit. The gas-permeable membrane 16 may be formed directly on the plug 19, though this is not shown. In addition, a common electrode can be installed in the Teflon tube 17.

<Experiment 2>

Figure 4:
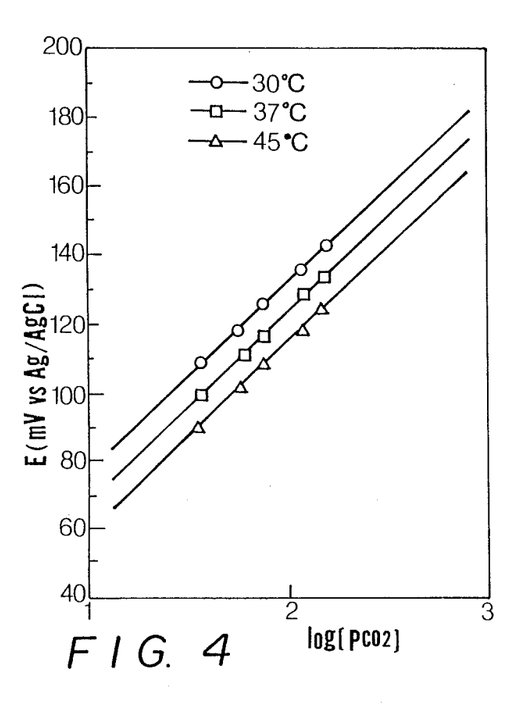
FIG. 4 is a graph illustrating the static characteristics of a gas sensor.

The characteristics of the carbon dioxide gas sensor fabricated in accordance with Example 6 were measured in a static system as follows: The gas sensor was dipped in an aqeuous solution of 10 mM sodium bicarbonate and 154 mM sodium chloride, and the potential across the electrodes when the partial pressure of carbon dioxide gas was varied was plotted against the common logarithm of the partial pressure. This was performed at the three temperatures of 30° C., 37° C. and 45° C. The results are as shown in FIG. 4.

A linear relationship showing good correlation between the measured electromotive force and logarithmic values of partial pressure was obtained at each temperature for carrbon dioxide gas partial pressures ranging from 20 to 250 mmHg.

Figure 5:
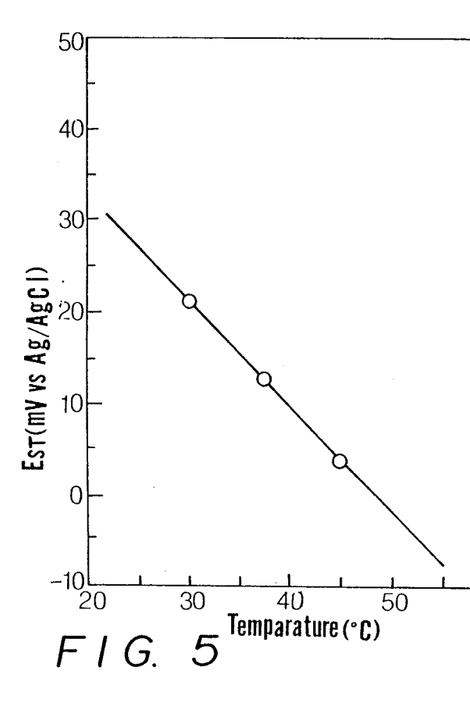
FIG. 5 is a graph illustrating the relationship between a standard potential $E_{ST}$ and temperature.

The recurrence formulae at respective temperatures were as follows:

30° C. $E/mV = 21.64 + 55.47 \log(pCO_2)$
37° C. $E/mV = 14.50 + 55.54 \log(pCO_2)$
45° C. $E/mV = 4.57 + 55.39 \log(pCO_2)$ These recurrence formulae show that the slope of the straight line exhibits almost no change despite the change in temperature, and that the constants exhibit a linear relationship with respect to temperature, as indicated in FIG. 5. Accordingly, it was found that the characteristics of the gas sensor of Example 6 can be expressed by Eq. (1), as follows:

$$E(mV) = a + bT + \text{slope} \log(pCO_2/ mmHg) \qquad (1)$$

where a, b and the slope are constants and T represents temperature (° C.).

Accordingly, in continuous monitoring, a temperature-compensated value of pCO2 can be measured based on the following equation:

$$\log[pCO_2/(mmHg)] = (E-a-bT)/\text{slope}$$

When the gas sensor is actually calibrated, it is required to determine a calibration formula, namely the coefficients a, b, slope, maintaining three-point correction. The calibration method will now be described with reference to FIG. 6.

Figure 6:
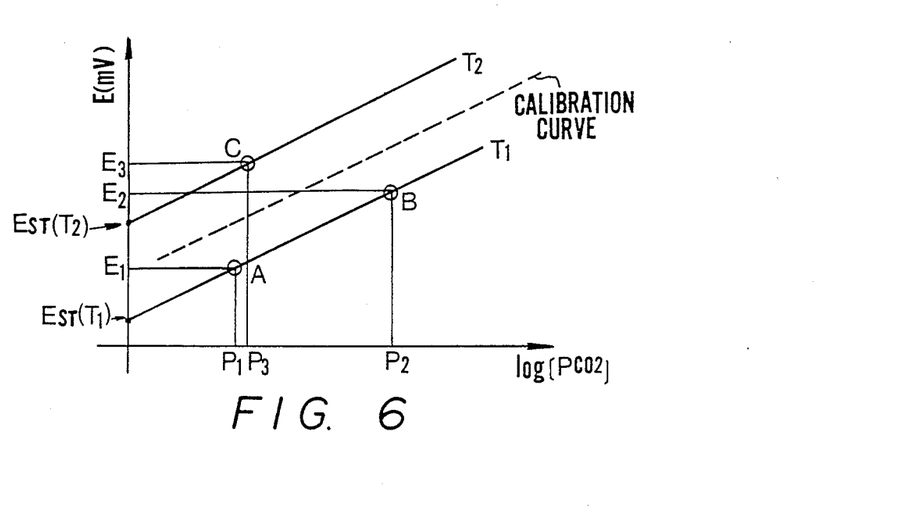
FIG. 6 is a graph useful in describing a calibration method.

A potential $E_1$ at point A, namely at a temperature $T_1$ and partial pressure $P_1$, a potential $E_2$ at point b, namely at a temperature $T_1$ and partial pressure $P_2$, and a potential $E_3$ at point C, namely at a temperature $T_2$ and partial pressure $P_3$ ($P_3 = P_1$) are measured, and a standard potential $E_{ST}(T_1)$ at the time of slope and temperature $T_1$ is determined from the values at the two points A, B. Further, a standard potential $E_{ST}(T_2)$ at the time of temperature $T_2$ is determined using the slope and value of $E_3$, and the coefficients a, b are obtained from the values of $T_1$, $E_{ST}(T_1)$, $T_2$, $E_{ST}(T_2)$. The calibration formula (1) is then formed.

Actual values used in calibration are as follows:
Point A: $T_1 = 37°$ C., $P_1 = 35.4$ mmHg, $E_1 = 100.0$ mV
Point B: $T_1 = 37°$ C., $P_1 = 72.1$ mmHg, $E_1 = 115.3$ mV
Point C: $T_2 = 30°$ C., $P_1 = 36.2$ mmHg, $E_1 = 109.0$ mV From calculation, $a = 70.24$, $b = -1.36$, slope $= 51.25$ are obtained.

<Experiment 3>

Figure 7:
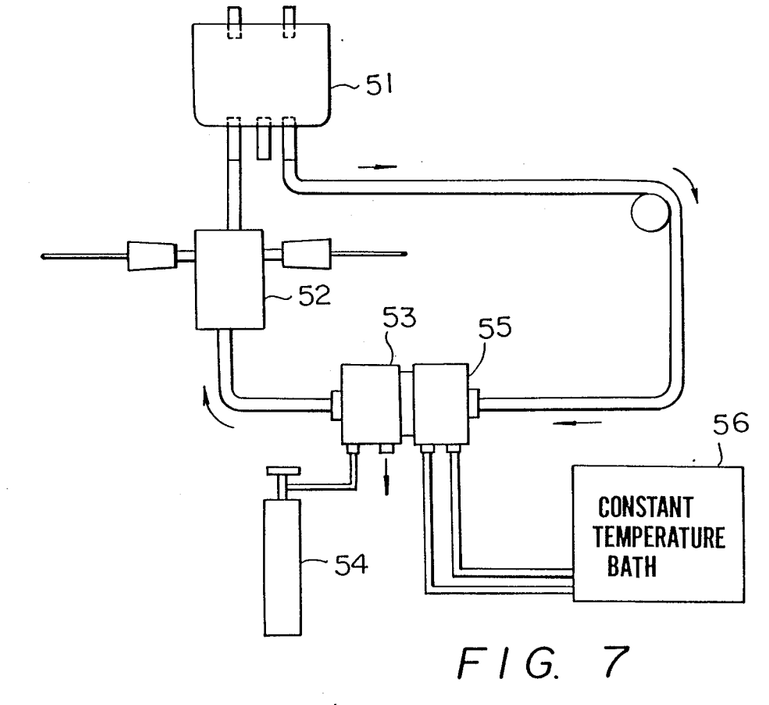
FIG. 7 is a schematic view of a circulating circuit used in measurement.

A gas sensor calibrated as set forth in Experiment 2 was installed in a circulating circuit of the kind shown in FIG. 7 and a continuous measurement was taken while varying partial pressure, temperature and the like. The circulating liquid was 500 ml of an aqueous solution containing 10 mM $NaHCO_3$ and 154 mM NaCl, and the liquid was circulated at a flow rate of 450 ml/min. Numeral 51 denotes a reservoir, 52 a flow cell, 53 a gas exhange equipment, 54 a gas cylinder, 55 a heat exchanger, and 56 a thermo-regulated bath (constant-temperature bath).

Figure 8:
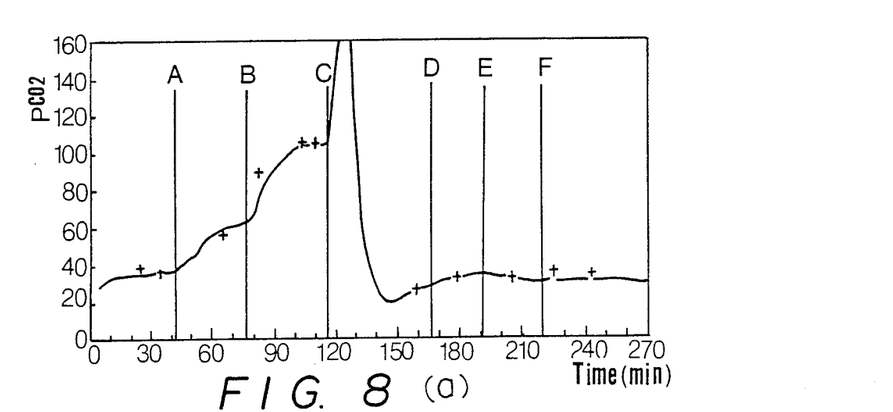
Figure 8B:
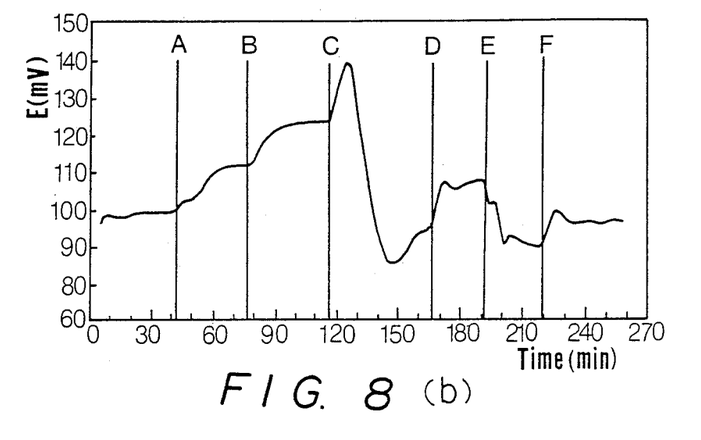
Figure 8C:
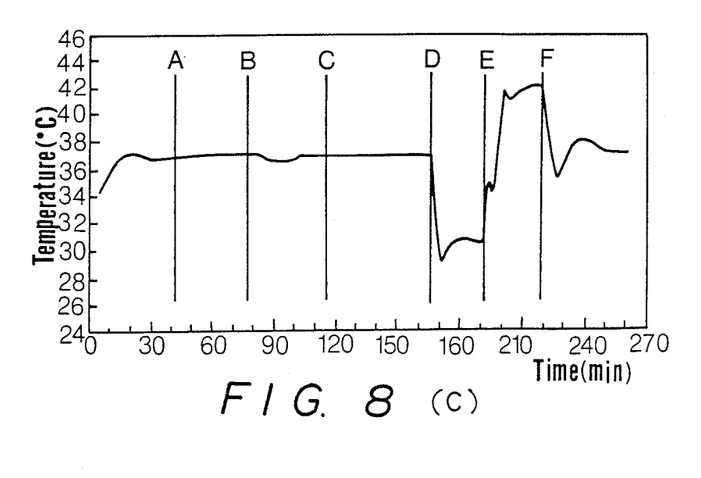

FIGS. 8 (a)-(c) are graphs of partial pressure vs. time, potential vs. time and temperature vs. time, respectively, illustrating the results of measurement. The "+" marks in (a) of FIG. 8 are values sampled and measured by a blood gas analyzer (ABL-30, manufactured by Radiometer). The aphabetic characters A, B, C are points at which temperature was held constant and partial pressure varied, while the alphabetic characters are points at which partial pressure was held constant and temperature varied.

In the interval where partial pressure is varied from the starting point to point D, values closely approximate the sampled values, in response to the change in partial pressure. Even in the interval from point D, where the temperature is changed, to the end point, the potential in interval D-E, example, is about the same as the potential in the interval A-B. The partial pressure values, however, do not take on the partial pressure values in the interval A-B, and these are in good agreement with the sampled values. Though this is a phenomenon in which there is a variation in potential accompanying a variation in temperature, the fact that a correct partial pressure value is indicated regardless of the change in potential means that the temperature compensation is being performed correctly.

It will be understood from the foregoing discussion that the gas sensor of the illustrated embodiment makes it possible to perform a continuous measurement, inclusive of a temperature compensation, using the above-described calibration method. Though Example 6 deals with a carbon dioxide gas sensor, it is obvious that the invention can also be applied to other gas sensors.

As many apparently widely different embodiments of the present invention can be made without departing from the spirit and scope thereof, it is to be understood that the invention is not limited to the specific embodiments thereof except as defined in the appended claims.

What we claim is:

1. A gas sensor comprising:
   a pH electrode which includes an electrically conductive substrate, a redox layer coating a surface of said electrically conductive substrate, and a hydrogen ion carrier layer coating a surface of said redox layer;
   a reference electrode;
   an insulating layer for insulating said pH electrode and said reference electrode;
   a gas-sensitive layer coating exposed surface portions of said pH electrode, said insulating layer and said reference electrode; and
   a gas-permeable layer coating a surface of said gas-sensitive layer.

2. The gas sensor according to claim 1, wherein said reference electrode comprises a silver having a silver chloride formed on a surface thereof.

3. The gas sensor according to claim 1, wherein said gas-sensitive layer comprises an aqueous solution of polyvinyl alcohol dissolved in a solvent which contains a salt derived from the interest gas.

4. The gas sensor according to claim 1, wherein said gas-permeable layer comprises a silicone membrane.

5. A gas sensor comprising:
   a pH electrode having a sensitive portion;
   a reference electrode having a sensitive portion; and
   a gas-permeable layer contacting the sensitive portion of said pH electrode and the sensitive portion of said reference electrode through the intermediary of a gas-sensitive solution or gel;
   said pH electrode further comprising:
   an electrically conductive substrate;
   a redox layer coating a surface of said electrically conductive substrate; and
   a hydrogen ion carrier layer, which is sensitive to a hydrogen ion concentration, coating said redox layer.

6. The gas sensor according to claim 5, further comprising a porous layer for maintaining a constant spacing between the sensitive portion of said pH electrode and said gas-permeable layer.

7. The gas sensor according to claim 5, wherein said reference electrode comprises:
   an agar-agar gel containing saturated sodium chloride partitioned by at least two barrier walls penetrated by a hollow fiber, and
   a silver/silver chloride electrode in said agar-agar gel.

8. The gas sensor according to claim 5, wherein said gas-sensitive solution comprises an aqueous solution of polyvinyl chloride dissolved in a solvent which contains a salt derived from the interest gas.

9. The gas sensor according to claim 5, wherein said gas-permeable layer comprises a silicone membrane.

10. A gas sensor comprising:
    a pH electrode having a sensitive portion;
    a reference electrode having a sensitive portion;
    a thermistor; and
    a gas-permeable layer contacting the sensitive portion of said pH electrode, the sensitive portion of said reference electrode and said thermister through the intermediary of a gas-sensitive solution;
    said pH electrode further comprising:
    an electrically conductive substrate;
    a redox layer coating a surface of said electrically conductive substrate; and
    a hydrogen ion carrier layer, which is sensitive to a hydrogen ion concentration, coating said redox layer.

11. The gas sensor according to claim 10, wherein said pH electrode further comprising a porous layer for maintaining a constant spacing between the sensitive portion of said pH electrode and said gas-permeable layer.

12. The gas sensor according to claim 10, wherein said reference electrode comprises:
   an agar-agar gel containing saturated sodium chloride partitioned by at least two barrier walls penetrated by a hollow fiber, and
   a silver/silver chloride electrode in said agar-agar gel.

13. The gas sensor according to claim 10, wherein said gas-sensitive solution comprises an aqueous solution of polyvinyl chloride dissolved in a solvent which contains a salt derived from the interest gas.

14. The gas sensor according to claim 10, wherein said gas-permeable layer comprises a silicone film.

* * * * *